US00PP21591P2

(12) United States Plant Patent
Wood

(10) Patent No.: US PP21,591 P2
(45) Date of Patent: Dec. 28, 2010

(54) ***HYDRANGEA* PLANT NAMED 'SHUGERT'**

(50) Latin Name: *Hydrangea macrophylla*
Varietal Denomination: Shugert

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/462,540

(22) Filed: Aug. 5, 2009

(51) Int. Cl.
*A01H 5/00* (2006.01)

(52) U.S. Cl. ..... Plt./250

(58) Field of Classification Search ..... Plt./250
See application file for complete search history.

(56) References Cited

PUBLICATIONS

Upov-rom GTITM Plant Variety Database 2010/03, GTI Jouve Retrieval Software, Citation for *Hydrangea* 'Shugert', one page.*

* cited by examiner

*Primary Examiner*—June Hwu
(74) *Attorney, Agent, or Firm*—C. A. Whealy

(57) ABSTRACT

A new and distinct cultivar of *Hydrangea* plant named 'Shugert', characterized by its upright and mounded plant habit; strong roots and stems; strong and dark green-colored leaves; early flowering habit; large lacecap-type inflorescences with light purple-colored flowers; and ability to reflower and to develop flowers on new growth without a cold treatment.

2 Drawing Sheets

Botanical designation: *Hydrangea macrophylla.*
Cultivar denomination: 'Shugert'.

BACKGROUND OF THE INVENTION

The present invention relates to a new and distinct cultivar of *Hydrangea* plant, botanically known as *Hydrangea macrophylla* and hereinafter referred to by the name 'Shugert'.

The new *Hydrangea* plant is a product of a planned breeding program conducted by the Inventor in Grand Haven, Mich. The objective of the breeding program was to develop new *Hydrangeas* with attractive foliage and flower coloration.

The new *Hydrangea* plant originated from an open-pollination during the summer of 2003 of the *Hydrangea macrophylla* 'Bailmer', disclosed in U.S. Plant Pat. No. 15,298, as the female, or seed parent and an unknown selection of *Hydrangea macrophylla*. The new *Hydrangea* plant was discovered and selected by the Inventor in May, 2005 as a flowering plant within the progeny of the stated open- pollination in a controlled outdoor nursery environment in Grand Haven, Mich.

Asexual reproduction of the new cultivar by softwood cuttings in Grand Haven, Mich. since June, 2005 has shown that the unique features of this new *Hydrangea* plant are stable and reproduced true to type in successive generations of asexual reproduction.

SUMMARY OF THE INVENTION

Plants of the new *Hydrangea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Shugert'.

These characteristics in combination distinguish 'Shugert' as a new and distinct cultivar of *Hydrangea:*

1. Upright and mounded plant habit.
2. Strong roots and stems.
3. Strong and dark green-colored leaves.
4. Early flowering habit.
5. Large lacecap-type inflorescences with light purple-colored flowers.
6. Ability to reflower and to develop flowers on new growth without a cold treatment.

Plants of the new *Hydrangea* differ primarily from plants of the female parent, 'Bailmer', in the following characteristics:

1. Plants of the new *Hydrangea* have larger sterile flowers than plants of 'Bailmer'.
2. Plants of the new *Hydrangea* are hardier than plants of 'Bailmer'.

Plants of the new *Hydrangea* can be compared to plants of 'Fasan', not patented. Plants of the new *Hydrangea* differ primarily from plants of 'Fasan' in the following characteristics:

1. Plants of the new *Hydrangea* will develop flowers on new wood and will reflower whereas plants of 'Fasan' only develop flowers on old wood and do not reflower.
2. Plants of the new *Hydrangea* have smaller inflorescences than plants of 'Fasan'.
3. Plants of the new *Hydrangea* are hardier than plants of 'Fasan'.

BRIEF DESCRIPTION OF THE PHOTOGRAPHS

The accompanying colored photographs illustrate the unique appearance of the new *Hydrangea* plant, showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'Shugert' grown in an outdoor nursery.

The photograph on the second sheet is a close-up view of a typical inflorescence of 'Shugert'.

DETAILED BOTANICAL DESCRIPTION

Plants used in the aforementioned photographs and in the following description were grown during the summer in Grand Haven, Mich. in ground beds in an outdoor nursery and under conditions which closely approximate commercial production conditions. Plants of the new *Hydrangea* were three years old when the photographs and description were taken. In the following description, color references are made to The Royal Horticultural Society Colour Chart, 1995 Edition, except where general terms of ordinary dictionary significance are used.

Botanical description: *Hydrangea macrophylla* 'Shugert'.

Parentage:

*Female, or seed, parent.*—*Hydrangea macrophylla* 'Bailmer', disclosed in U.S. Plant Pat. No. 15,298.

*Male, or pollen, parent.*—Unknown selection of *Hydrangea macrophylla*, not patented.

Propagation:

*Type cutting.*—By softwood cuttings.

*Time to initiate roots.*—About ten days at temperatures of about 24° C.

*Time to produce a rooted young plant.*—About 40 days at temperatures of about 24° C.

*Root description.*—Fine to thick, fibrous.

*Rooting habit.*—Freely branching; dense.

Plant description:

*Form/growth habit.*—Perennial shrub; upright and mounded plant habit; broadly inverted triangle; strong lateral branches; vigorous growth habit.

*Plant height.*—About 62 cm.

*Plant diameter or area of spread.*—About 78 cm.

*Branching habit.*—When pinched, freely branching with about 48 lateral branches per plant.

*Lateral branches.*—Length: About 52 cm. Diameter: About 7 mm. Internode length: About 6.5 cm. Texture: Smooth, glabrous. Strength: Strong. Color, young: Close to 144B. Color, older: Close to 199B.

Foliage description:

*Arrangement.*—Opposite, simple.

*Length.*—About 14.5 cm.

*Width.*—About 10 cm.

*Shape.*—Elliptical.

*Apex.*—Acuminate to acute.

*Base.*—Cuneate to obtuse.

*Margin.*—Serrate.

*Texture, upper and lower surfaces.*—Smooth, glabrous.

*Venation pattern.*—Pinnate.

*Color.*—Developing leaves, upper surface: Close to 137B. Developing leaves, lower surface: Close to 137C. Fully expanded leaves, upper surface: Close to 137A; venation, close to 143C. Fully expanded leaves, lower surface: Close to 137C; venation, close to 143C.

*Petiole.*—Length: About 4.3 cm. Diameter: About 4 mm Texture, upper and lower surfaces: Smooth, glabrous. Color, upper and lower surfaces: Close to 143C.

Flower description:

*Flower type and habit.*—Single sterile and fertile flowers arranged on terminal lacecap-type panicles; flowers face upright or outwardly.

*Fragrance.*—Not detected.

*Natural flowering season.*—Continuous flowering from June to September in Grand Haven, Mich.; early flowering habit; plants will develop flowers on new growth and will reflower.

*Flower longevity, fertile flowers.*—Flowers last about three to four weeks on the plant and about 10 to 20 days as a cut flower; flowers not persistent.

*Flower longevity, sterile flowers.*—Flowers last about four to five months on the plant and about one month as a cut flower; flowers persistent.

*Quantity of flowers.*—Freely flowering; about 365 fertile flowers and about 16 sterile flowers per panicle.

*Panicle height.*—About 5.1 cm.

*Panicle diameter.*—About 15 cm.

*Flower diameter, fertile flowers.*—About 6 mm.

*Flower depth (height), fertile flowers.*—About 4 mm.

*Flower diameter, sterile flowers.*—About 5.5 cm.

*Flower depth (height), sterile flowers.*—About 5 mm.

*Flower buds, fertile and sterile flowers.*—Length: About 4 mm. Diameter: About 4 mm. Shape: Globose. Color: Close to 62B.

*Petals, fertile flowers only.*—Quantity/arrangement: Four in a single whorl. Length: About 3 mm. Width: About 2 mm. Shape: Lanceolate, cupped. Apex: Acute. Base: Attenuate. Margin: Entire. Texture, upper and lower surfaces: Smooth, glabrous. Color: When opening, upper surface: Close to 62B. When opening, lower surface: Close to 62C. Fully opened, upper and lower surfaces: Close to 76C; color becoming closer to 79C with development.

*Sepals, fertile flowers.*—Quantity/arrangement: Five in a single whorl. Length: About 0.5 mm. Width: About 1 mm. Shape: Roughly deltoid. Apex: Acute. Base: Fused. Margin: Entire. Texture, upper and lower surfaces: Smooth, glabrous. Color, upper and lower surfaces: Close to 144D.

*Sepals, sterile flowers.*—Quantity/arrangement: Four in a single whorl. Length: About 2.2 cm. Width: About 2.3 cm. Shape: Broadly ovate. Apex: Broadly obtuse. Base: Obtuse. Margin: Entire. Texture, upper and lower surfaces: Smooth, glabrous. Color: When opening and fully opened, upper surface: Between 76A and 81C. When opening and fully opened, lower surface: Between 76D and 81D.

*Peduncles, fertile and sterile flowers.*—Angle: Erect to about 30° from vertical. Strength: Strong. Length: About 5.2 cm. Diameter: About 5 mm. Texture: Smooth, glabrous. Color: Close to 144B, random specks, close to 59A.

*Pedicels, fertile flowers.*—Angle: About 10° to 20° from vertical. Strength: Strong. Length: About 5 mm. Diameter: About 1 mm. Texture: Smooth, glabrous. Color: Close to 75D.

*Pedicels, sterile flowers.*—Angle: About 10° to 20° from vertical. Strength: Strong. Length: About 2 cm. Diameter: About 2 mm. Texture: Smooth, glabrous. Color: Close to 75D.

*Reproductive organs, fertile flowers only.*—Stamens: Quantity per flower: About five. Anther length: About 1.5 mm. Anther shape: Oblong. Anther color: Close to 66C. Pollen amount: Moderate. Pollen color: Close to 198C. Pistils: Pistil quantity per flower: About two or three. Pistil length: About 2 mm. Stigma shape: Biparted. Stigma color: Close to 66D. Style length: About 2 mm. Style color: Close to 66D. Ovary color: Close to 74C.

*Seeds.*—Quantity per inflorescence: Numerous; dust-like. Size: Less than 0.1 mm by less than 0.1 mm. Color: Close to 200D.

Disease/pest resistance: Plants of the new *Hydrangea* have not been observed to be resistant to pathogens and pests common to *Hydrangea*.

Temperature tolerance: Plants of the new *Hydrangea* have been shown to be tolerant to temperatures ranging from about −27° C. to about 37° C.

It is claimed:

1. A new and distinct *Hydrangea* plant named 'Shugert' as illustrated and described.

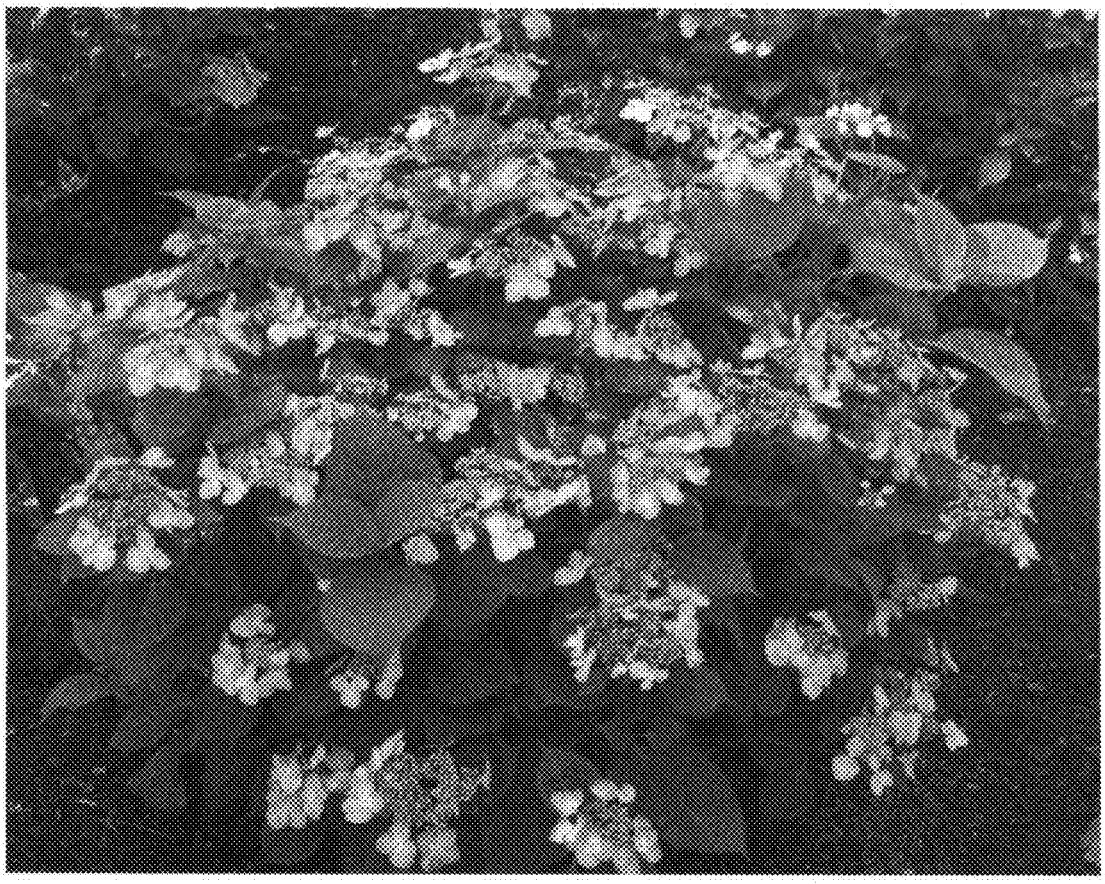

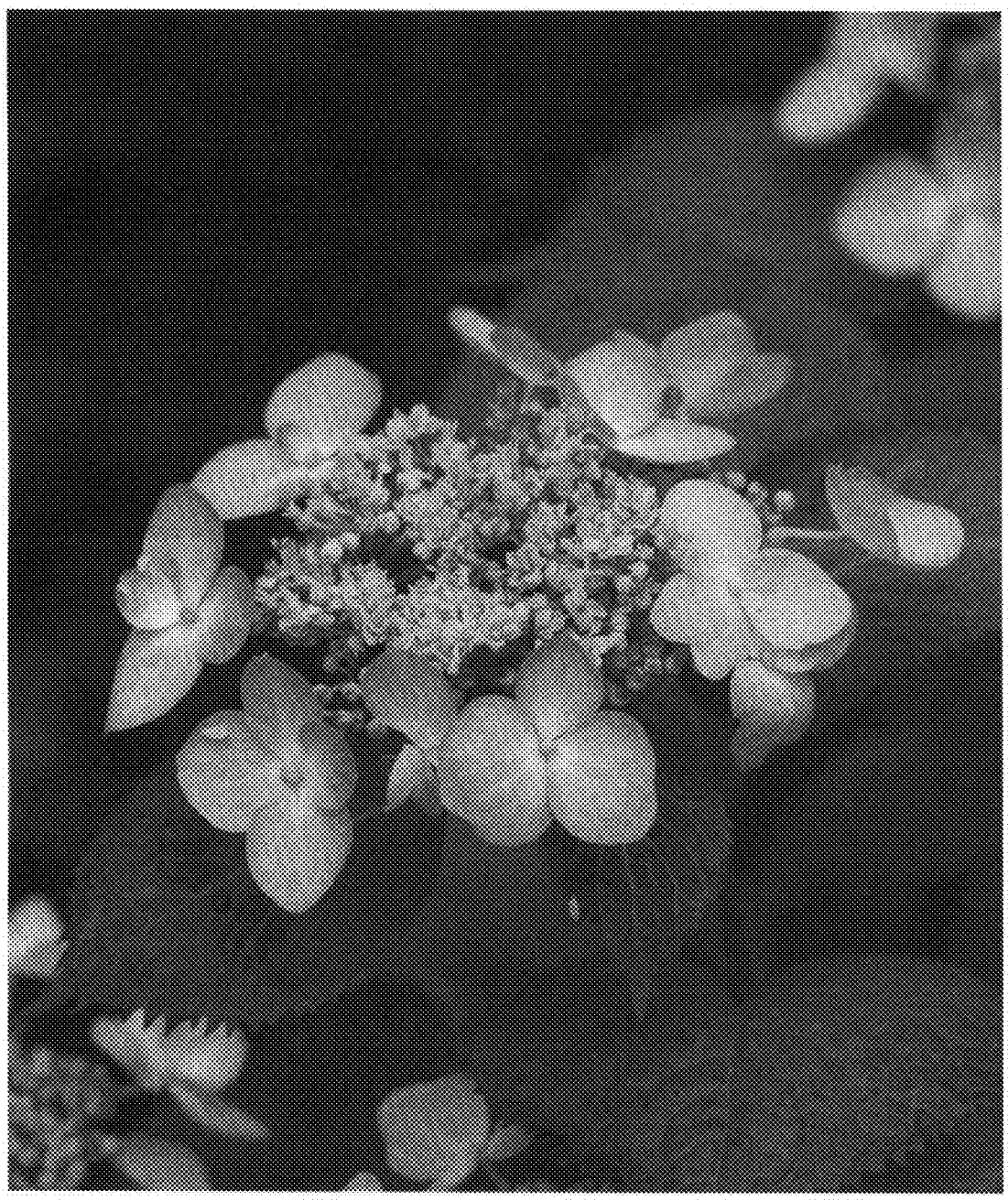

* * * * *